US007264356B2

(12) United States Patent
Jones et al.

(10) Patent No.: US 7,264,356 B2
(45) Date of Patent: Sep. 4, 2007

(54) TECHNIQUES FOR DIAGNOSING AND AIDING COLOR VISION (75) Inventors: Peter W. J. Jones, Belmont, MA (US); Dennis W. Purcell, Medford, MA (US)

(73) Assignee: Tenebraex, Inc., Boston, MA (US)

( * ) Notice: Subject to any disclaimer, the term of this patent is extended or adjusted under 35 U.S.C. 154(b) by 236 days.

(21) Appl. No.: 10/912,835

(22) Filed: Aug. 6, 2004

(65) Prior Publication Data

US 2005/0105051 A1 May 19, 2005

Related U.S. Application Data (60) Provisional application No. 60/493,205, filed on Aug. 6, 2003.

(51) Int. Cl.
 A61B 3/02 (2006.01)
 A61B 3/00 (2006.01)
(52) U.S. Cl. .............. 351/242; 351/200; 351/239; 351/246; 345/589; 345/591
(58) Field of Classification Search ........... 351/200, 351/222, 239, 242, 243, 246; 345/418, 589, 345/591, 593; 348/62, 649, 651, 659; 382/254, 382/260, 167
See application file for complete search history.

(56) References Cited

U.S. PATENT DOCUMENTS

| 1,616,604 | A | | 2/1927 | Brophy |
| 5,589,898 | A | * | 12/1996 | Atkinson ............ 351/237 |
| 5,898,381 | A | | 4/1999 | Gartner et al. |
| 6,054,932 | A | | 4/2000 | Gartner et al. |
| 6,210,006 | B1 | * | 4/2001 | Menozzi ............ 351/242 |
| 6,211,779 | B1 | | 4/2001 | Gibb et al. |
| 6,306,459 | B1 | | 10/2001 | Fleming |
| 6,340,868 | B1 | | 1/2002 | Lys et al. |
| 6,345,128 | B1 | * | 2/2002 | Stokes ............ 382/254 |
| 6,461,008 | B1 | | 10/2002 | Pederson |
| 6,591,008 | B1 | * | 7/2003 | Surve et al. .......... 382/162 |
| 6,729,729 | B1 | * | 5/2004 | Irons ............ 351/242 |
| 6,769,138 | B2 | | 8/2004 | Golle et al. |
| 6,851,809 | B1 | * | 2/2005 | Sachtler ............ 351/242 |
| 2002/0145805 | A1 | | 10/2002 | Hall |
| 2003/0095705 | A1 | * | 5/2003 | Weast ............ 382/167 |
| 2004/0056965 | A1 | * | 3/2004 | Bevans et al. ......... 348/222.1 |
| 2004/0085327 | A1 | | 5/2004 | Jones et al. |
| 2004/0212815 | A1 | * | 10/2004 | Heeman et al. ........ 358/1.9 |
| 2005/0152141 | A1 | | 7/2005 | Traynor |

FOREIGN PATENT DOCUMENTS

JP 10003596 1/1998

* cited by examiner

*Primary Examiner*—Ali Imam
*Assistant Examiner*—John R Sanders
(74) *Attorney, Agent, or Firm*—Fish & Neave IP Group, Ropes & Gray LLP (57) ABSTRACT

Systems and methods for determining and addressing color-vision impairment by allowing a patient to compare multiple images of a scene wherein the color content of selected ones of the images has been manipulated by altering a portion of the color space that is less detectable to a person having a particular type of color vision impairment.

16 Claims, 11 Drawing Sheets

WHICH PICTURE BELOW LOOKS THE MOST LIKE THE COLOR OF THIS PICTURE?

TECHNIQUES FOR DIAGNOSING AND AIDING COLOR VISION

CLAIM OF PRIORITY

This application claims the benefit of the earlier filed Provisional Application filed 6 Aug. 2003 and having Ser. No. 60/493,205, the contents of which are hereby incorporated by reference.

BACKGROUND

Figure 1:
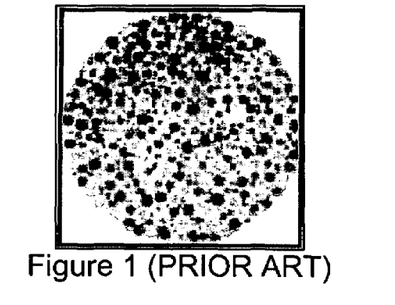
FIG. 1 illustrates a prior art test for color vision.

Testing for color vision problems is traditionally done by means of the Ishihara test (there are other more accurate tests, but they require very expensive equipment). The Ishihara test consists of a series of plates made up of variously colored dots. Numbers are formed by dots of different colors. One example of an Ishihara test is given in FIG. 1. For purposes of illustration, FIG. 1 presents the example Ishihara test in grey scale. However in actual practice this familiar test is a color image that comprises a plurality of colored dots that are arranged on the plate so that certain colored dots form an image, typically the image of a number. On certain plates, the colors that form the numbers are impossible for color blind people to separate from the background dots' colors. A series of different plates is used in the diagnostic process and by noting which plates the test subject successfully identifies or misses, a diagnosis of normal vision or of specific kinds of color impairments can be made.

Many color-vision impaired people speak with anger or strong aversion to the Ishihara test. They feel like the test determines whether you can see some "some secret code." The correct numbers are something that "normal" people can see, but that you as a color blind person are left out. Their memories of the testing process are often recalled with a sense of embarrassment or shame.

Additionally, the animosity that patients feel toward these traditional test often manifests itself as antipathy toward the test and a lack of effort in trying to answer the test questions correctly. Accordingly, there is need in the art for improved systems and methods for testing for color vision impairment.

SUMMARY

To this end, the systems and methods described herein provide, among other things, software tools that manipulate normal color images to reduce the information content to what a color-vision impaired person would see. The systems and methods test for color vision effectiveness and provide methods for treating and aiding the development of color vision.

More particularly, the systems and methods described herein include a method for testing for color-impaired vision, that comprises providing a reference image depicting a scene presented in colors selected from a selected color space, identifying an isochromatic line within the color space and being associated with a color vision impairment, generating a first test image depicting the scene of the first image presented with a color space modified to move hues along the isochromatic line, generating a second test image depicting the scene of the first image with a color space modified to move hues away from the isochromatic line, and having a patient make a visual comparison among the reference image and the first and second test images.

Optionally, the method further comprises directing the patient to compare the reference image to the first and second test images and select the test image that appears most similar, or least similar, to the reference image. Further optionally, the method may comprise the operation of generating a grey scale image of the scene and presenting the grey scale image to the patient for comparison, and reordering the presentation of the first and second test images and having the patient repeat the visual comparison. The reordering may be done randomly. For example, the method may randomly reorder the first and second test images, repeatedly have the patient make the visual comparison, and determine how often the visual comparison yields similar results. The number of test or answer images may vary and the method may generate additional test images and have the patient visually compare the additional test images to the reference image, as desired or appropriate.

Identifying the isochromatic line may include identifying an isochromatic line associated with a known type of color-vision, such as an isochromatic line associated with deuteranopia or an isochromatic line associated with protanopia. Further, the method may include identifying isochromatic line by randomly selecting an isochromatic line that extends at least partially through the color space.

When generating a first test image, the process may generate the first test image with a color space modified to move hues along the partial isochromatic line. The method may determine whether the patient can perceive colors along the selected partial isochromatic line, and generate a plurality of partial isochromatic lines for constructing a line of color confusion for the patient. Optionally, the method may determine a blocking filter for increasing a separation between a first set of wavelengths and a second set of wave lengths, and apply the blocking filter to color images presented to the test taker and provide clues as to the colors being presented.

In another aspect, the invention provides a test for color vision and systems for testing for color impaired vision. The systems may comprise a reference image depicting a scene presented in colors selected from a selected color space, an image processor for identifying an isochromatic line within the color space and for generating a first and second answer image having colors selected as a function of the isochromatic line, and a display for displaying the reference image and the first and second answer images to a test taker. The image processor may include a process for altering colors in the reference image by moving to hues along the isochromatic line or moving to hues off of the isochromatic line. The system may generate the blocking filter for providing the test taker with images having a color space heightened for their respective type of color vision.

BRIEF DESCRIPTION OF THE DRAWINGS

The foregoing and other objects and advantages of the invention will be appreciated more fully from the following further description thereof, with reference to the accompanying drawings wherein.

DESCRIPTION OF CERTAIN ILLUSTRATED EMBODIMENTS

To provide an overall understanding of the invention, certain illustrative embodiments will now be described for diagnosing and aiding color vision detection. More specifically, certain exemplary methods will be described that generate multiple images of a scene, wherein the graphical scene in each image is the same or similar, but the coloring varies in a controlled manner. More particularly, the different colorings can be selected so that, for certain associated types of color-vision, these differently colored images will be perceived as similarly colored. This allows the patient to give a positive answer, stating that they see a similiarity between two images. Thus in certain embodiments, the systems and methods described herein provide a test that does not rely on the subject seeing or not seeing some "hidden image." Such tests described herein should also be more accurate under varying test conditions. The systems and methods discussed below are provided as illustrative of the invention and it will be understood by one of ordinary skill in the art that the systems and methods described herein can be adapted and modified and that such other additions and modifications will not depart from the scope hereof.

Figure 2A:
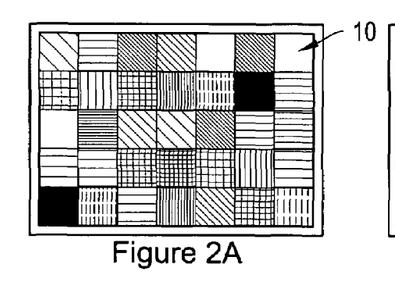
FIGS. 2A and 2B depict a first color image and a second color image generated by manipulating the colors in the first image.
Figure 2B:
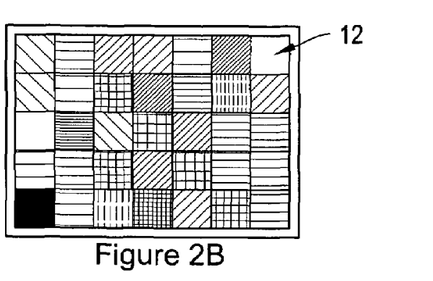

To this end, and for certain embodiments, the systems and methods described herein provide software tools for color blind users, that are capable of manipulating normal color images to reduce the information content to what a red/green color-vision impaired person would see. A first example of such a set of images is depicted in FIGS. 2A and 2B, that show a normal color image 10 and second, an image 12 that has been manipulated by removing the red/green information axis: When shown such a pair of images alternately to a red/green color-vision impaired person, studies show that the person knows that something is changing, but does not know what it is. It is a realization of the invention, that this effect may be the basis of an improved color vision test. In such a color vision test, the test giver provides a series of test frames that have a reference image, such as a full-color image, and a number of other manipulated answer images. The test subject, or patient, is asked to select from among the answer images the one that most closely matches the reference image. This makes the color vision test a positively framed, multiple choice test rather than the negatively framed Ishihara test (colored, numbers the test taker cannot see).

Figure 3:
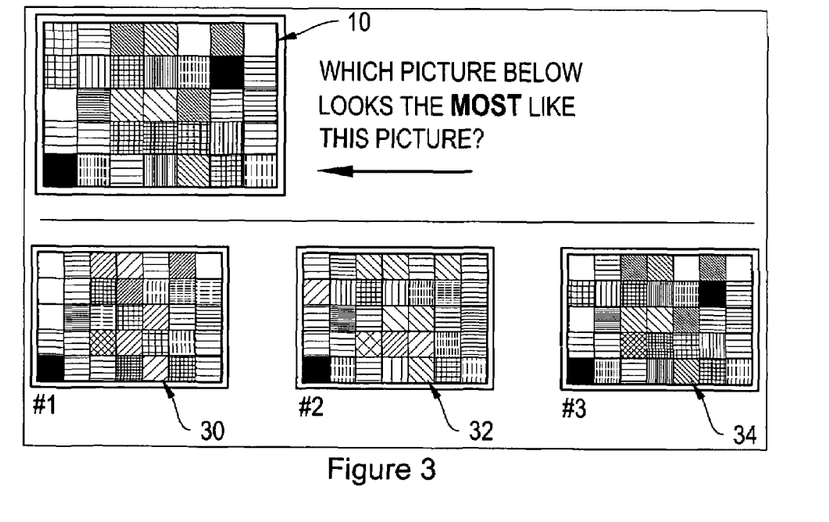
FIG. 3 depicts one embodiment of a color vision test according to the invention.
Figure 4A:
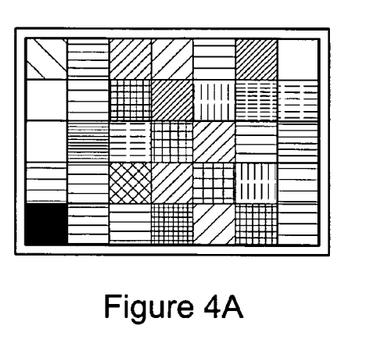
FIGS. 4A and 4B depict color images that have been modified to represent how a color reference image is perceived by a person having a particular type of color vision.
Figure 4B:
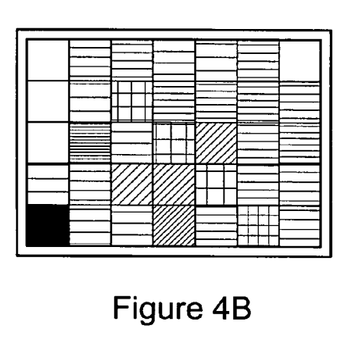

In the test described above and depicted in the FIG. 3, choice 1 is an image 30 manipulated by removing the red/green axis, and thus is how a red/green color vision sighted person sees the reference image 10. Choice 2 is the color image 32 with an overall blue cast added. Choice 3 is a gray-scale image 34 of the reference image 10. In certain practices and applications, a person with normal color vision will see image 32 as closest to the reference image 10 since image 32 is still a full-color image and people with typical color vision are used to seeing images with different color casts. Choice 3, image 34, is there as a place holder that neither color vision impaired or normally sighted subjects will pick. It is was predicted that a red/green color vision sighted person would pick image 30, and this result occurred in a test. FIGS. 4A and 4B illustrate how a person with red/green color vision sees the reference image 30 and choice 2, image 32. Specifically, the reference image looks like FIG. 4A to a red/green color vision sighted person: while choice 2 image 32 looks like FIG. 4B. The slight blue tint added to the full color image becomes much more prominent when seen by a red/green color vision sighted person because for that person, the red and green information is merged to yellow information only.

Figure 5:
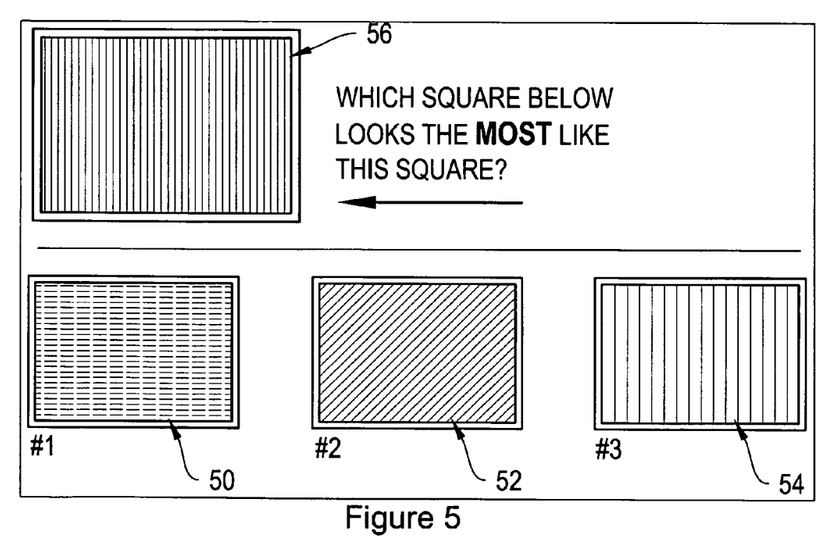
FIG. 5 depicts one embodiment of a color vision test according to the invention.

Another test frame shown in FIG. 5 uses simple color squares. Choice 1, image 50, is gray scale, and choice 2, image 52, is the reference image 56 manipulated to remove the red/green axis and choice 3, image 54 is the reference image 56 with a blue overall tint added. Again, our test subject said the choice 2, image 52, looked like the reference image 56.

The tests depicted in the above figures may be carried out on a conventional data processing platform, such as an IBM PC, a handheld computer or PDA, or a proprietary device that may be provided as test station for use in a doctor's office or a school. In one embodiment, the test method is realized by executing a computer program that includes a set of reference images. The images may be data files stored on a computer, or images printed to paper. Computer image files may be in any format, such as the GIF, JPEG, TIFF, PBM, PGM, PPM, EPSF, X11 bitmap, Utah Raster Toolkit RLE, PDS/VICAR, Sun Rasterfile, BMP, PCX, PNG, IRIS RGB, XPM, Targa, XWD, possibly PostScript, and PM formats. The image files can be stored in any suitable database system, including the commercially available Microsoft Access databas. The design and development of suitable database systems are described in McGovern et al., A Guide To Sybase and SQL Server, Addison-Wesley (1993). The database can be supported by any suitable persistent data memory, such as a hard disk drive, RAID system, or any other suitable system. The program may select a first one of the reference images from the database. An image processing module of the program may alter the color space that occurs in the reference image to generate one or more answer images, such as the answer images 30–34 depicted in FIG. 3.

The program may then generate a composite test page that includes the reference image and the answer images. One such example of this is depicted in FIG. 3, where the test page includes the reference image 10 and the three answer images 30, 32 and 34. The program may display the composite test page to the test taker and provide a prompt, such as a tone or an on screen message that directs the test taker to make a visual comparison between the reference image 10 and the answer images 30–34. The visual comparison may be to identify which answer image 30–34 is most similar to the reference image 10. Alternatively, the visual comparison may ask which answer image has the most similar colors or which is the least similar to the reference image 10. The visual comparison to be made can vary and any suitable comparison that provides data useful for determining the color vision of the test taken may be employed. The program may allow the test taken to enter an answer representative of the result of the comparison, such as by using the keyboard or mouse to indicate that choice 1, image 32 is the most similar image according to the test taker. The program may record the input and answer. In an optional practice the program may repeat the process described above several times, optionally rearranging the order in which the answer images 30–34 are presented on the test page. Each answer can be collected and the program may tally the number of time the test taker selected a respective one of the answer images. This provides data that can be evaluated to determine whether the test taker has a color vision that is associated with the condition being tested for. Optionally, based on the results of the test, the program may commence a second test by generating a new test page with answer images generated to test for a different type of color vision. One technique for generating the test images is described below.

The systems and methods described herein provide powerful diagnostic tools for determining a person's color vision. Without being bound by theory, one way of understanding the present systems and methods is that a person with normal color vision can distinguish all the colors that are depicted on a standard CIE (1931) diagram of color space. A common way of describing a person with impaired color vision is by means of so called "lines of confusion" (LOC). These are a series of lines superimposed on a standard CIE (1931) diagram such that to a person with a certain color vision deficiency, colors that lie along any of the LOC are indistinguishable. A common depiction of the LOC of a person with deutan red/green color vision (deuteranopia) is as shown in this FIG. 6. For example a greenish color A lying on LOC B is indistinguishable from a reddish color C, as shown in FIG. 7.

Figure 6:
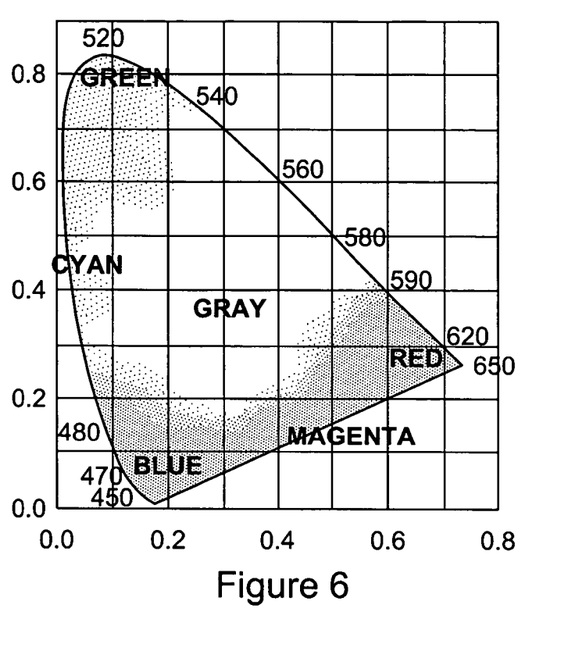
FIG. 6 depicts a standard CIE diagram of color space.
Figure 7:
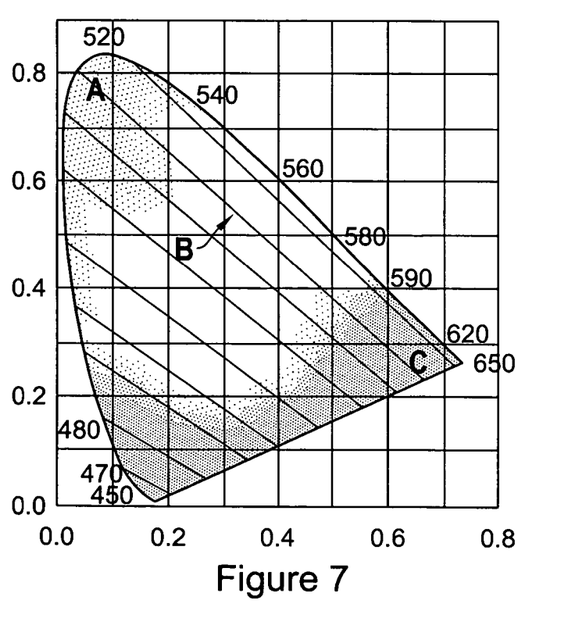
FIG. 7 depicts a set of lines of color confusion overlaying the color space of FIG. 6.

FIG. 6 is a commonly understood diagram of normal color space: the C.I.E. chromaticity diagram (1931). In this representation, there is only hue shown, not lightness/darkness (value) or saturation. A normally-sighted person can differentiate between all the colors represented in this diagram. In terms of this color space representation, for a color blind person there are lines of "color confusion" or "isochromatic lines". Colors (hues) that lie on one of these lines or vectors cannot be differentiated from one another. For example, if a certain red and a certain green both lie on a line or vector of color confusion, they cannot be differentiated one from another. Different forms of color vision have different lines or vectors of color confusion. According to the literature, there seems be not a few, but rather many variations in these lines or vectors of color confusion among color blind people. This is depicted by FIG. 7. It is difficult or impossible to choose one or even a few solutions for color display modifications that will work for all color blind people, even those nominally of the same type. Thus, the systems and methods described herein provide non-confrontational color vision tests that can test for each type of color vision, optionally walking through a decision tree as data is gathered to speed the test.

The test methods, in one practice, consist of presenting a series of one or more image sets to the test subject. These image sets consist of a reference image and two or more answer images. The images may be shown on a composite test page, as in FIG. 3, or sequentially one answer image after another. In each case, the subject is to choose the answer image that appears most similar to the reference image.

In one example, a full color reference image is to be matched with one of three match images. Preferably, the match or answer images are generated through a process that creates a set of answer images likely to determine the test taker's color vision. In one such process, for the first match image, colors from the original reference are along the LOC towards the center of the LOCs for a certain kind of color vision. In the second match image, the colors are displaced by the process slightly perpendicularly to the LOCs. In the third match image, the colors are desaturated by the process to grays. To a test subject with normal vision, the second match image generated by the process will look most similar to the reference image, since the match image will look like the reference image with a slight color cast (in this case bluish or yellowish). The first match image will look substantially different, since the colors will have all been reduced to various shades of yellow and blues. The third match image will also look different, since it is made up of grays.

The process for generating the test images may be realized as a computer program operating on a data processing system. Such processes for adjusting the color map or pallette of an image are well known in the art and described for example in Meyer, G. W. & Greenberg, D. P. (1988) 'Colour defective vision and computer graphic displays', IEEE Computer Graphics and Applications 8(5) 28–40.

To a test subject with color vision of the sort this frame is testing for, the first match image will look most similar to the reference image, since the colors that make up the reference image have all been replaced with other colors lying on the LOCs (and any colors that lie on a LOC for certain kind of color vision are indistinguishable by a person with that kind of color vision). The second match image will look different to the color blind person, since the colors will have been replaced by colors that are not on the LOCs, and thus look different. The third match image will look different, too, since it is made up of grays.

Figure 8A:
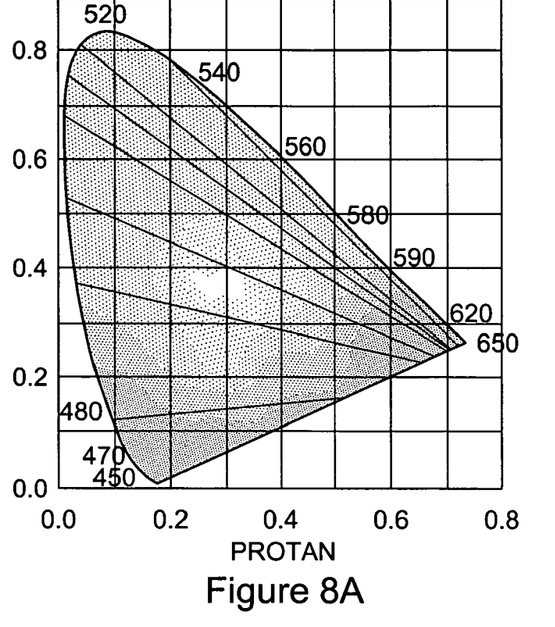
FIGS. 8A and 8B depict lines of color confusion for protan and deutan color vision.
Figure 8B:
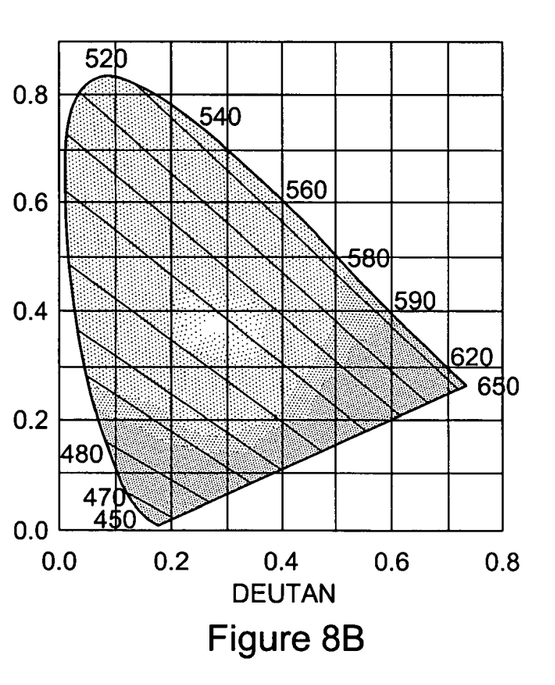

In another example, a test image set is selected to diagnose what kind of color vision a test subject has, for example, deuteranopia or protanopia. This test set may be presented to test subjects who have already been diagnosed as having red/green color vision. As shown in FIGS. 8A and 8B, the LOCs of deuteranopia and protanopia differ.

For example, for a deutan, the LOC in FIG. 8B that runs through a certain magenta also runs through a cyan green and a gray. For a protan, the LOC is FIG. 8A that runs through the same magenta runs instead through purples and a deep blue. In this image set, the reference image consists of a magenta patch. The match images, in this example may be, one, a cyan green and, two, a deep blue. For the deutan, the cyan green match will look the most similar to the reference image. For the protan, the deep blue match will look most similar to the reference image.

Note that in certain optional embodiments, this test may be incorporated into a single test set that would both diagnose color blindness and what kind of common variation of color vision the subject had in further optional embodiments, there are provided ways to prevent or detect cheating by test subjects. A test subject might seek to cheat the test by picking the image that does not look like the reference image. In one example, this can be detected by an image set that offers the test subject a color reference and two match images. The first match image is essentially the same as the reference image. The second match image has the referenced image's colors changed for colors that do not lie on LOCs. If the test subject chooses the second image, then the assumption is that he/she is trying to cheat the test.

There are certain mild forms of color blindness. For example, anomalous protans and anomalous deutans can successfully identify saturated colors (those that lie around the periphery of the CIE (1931) diagram), but have difficulty distinguishing less saturated colors (those that lie near the center of the diagram). These can be diagnosed by a variation of the first test image set described above, where the reference and match image colors consist only of less saturated colors that lie nearer to the center of the CIE (1931) diagram.

With a computer based test as described herein, order of the match images in the image sets can be randomized so that test subjects cannot learn by rote the correct answers. With a computer based test, test result data can be gathered by the program and periodically uploaded to a central point to aid in color vision research. For reasons of medical privacy concerns, individual personal identifiers can be stripped from the data. Furthermore, with a computer based test, new test image sets can be downloaded to the test locations and integrated into the test protocol, thus allowing new vision tests and research goals to be added inexpensively and easily.

A variety of complex images can be used for the reference images: from complex pictures to simple color squares. Additionally, because Ishihara test depends on subtle color difference to give a diagnosis, it is very susceptible to color shifting with age or the color temperature of the viewing light. In fact, if used under fluorescent lights or even regular incandescent bulbs the Ishihara tests are not accurate. In certain embodiments, of the systems described herein are computer based (preferably) and much less susceptible to being affected by color shifts (or certainly viewing lights).

For more sophisticated test protocols—to determine what kind of red/green color vision a subject has, for example—a calibration routine may be employed to adjust the program to work on any monitor these tests look at the relative brightness of red and green areas, and as such the program or monitor would be adjusted to normalize the relative brightness of the red and green pixels of each monitor.

Figure 9:
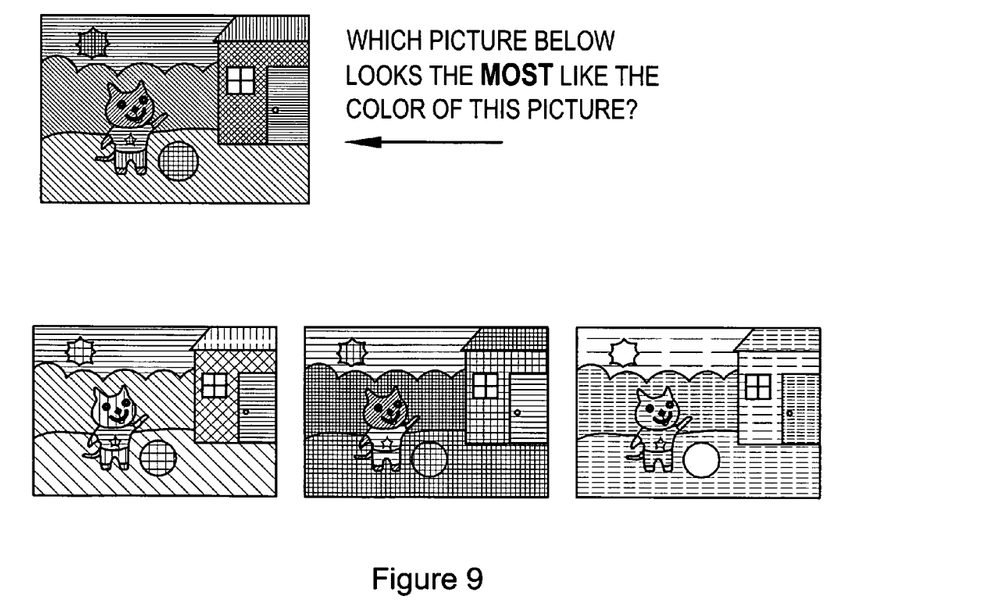
FIG. 9 depicts an alternative test page.
Figure 10:
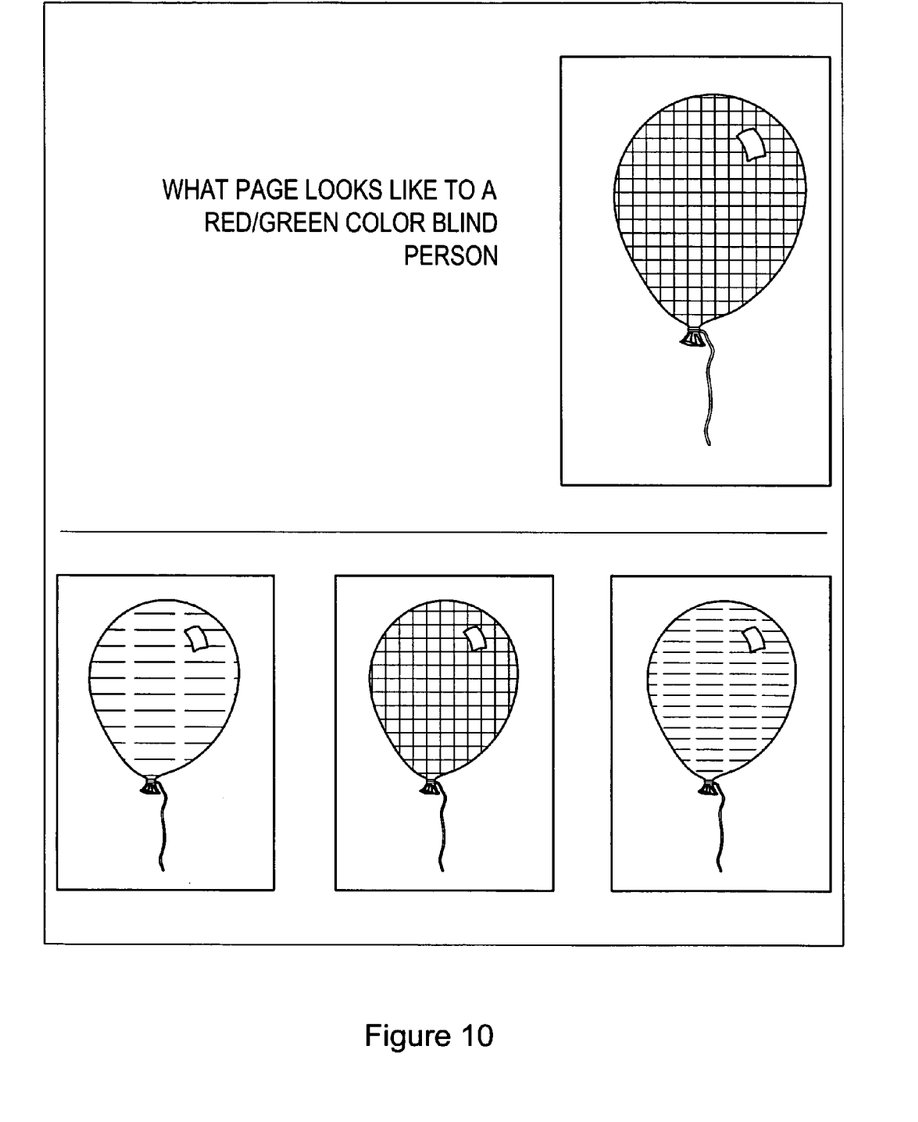
FIG. 10 depicts a further example of a test page.

FIG. 9 illustrates a set of examples of test drawings that may be used to test children in a less confrontational manner. To this end, FIG. 9 illustrates four cartoon pictures, each depicting the same scene. The image at the top is the reference image and the three images at the bottom are images that have been manipulated by altering the red/green axis, as described above. It is believed that by allowing a test taker (the child) to select an answer by making comparisons and choosing among his options, the child will feel less put upon then having to search for an image that is—to the color vision impaired—hidden away within an image.

The processes and systems described above are only examples and other techniques for carrying out the invention may be employed. For example, the process may use reference images and then manipulated versions of the reference images such as by filling the "A" channel in a LAB format with a 50% gray to merge the red and green information (or the red and blue information to diagnose other kinds of color vision). The process may add color casts to full-color images in the choice category to make an image shift that appears small to a normally sighted person but a large change to a color blind person. Further optionally, the process may add gray-scale choices to catch color blind subjects trying to cheat the test, knowing that a "full color" image that is shifted to blue can look gray to red/green color blind subjects. The process described above allow for diagnosing the different kinds of red/green color blind subjects ("red deficient" and "green deficient") by testing a red or green reference square with choices of lighter and darker choices of the manipulated LAB version of the full-color image. Optionally, the program may randomly shuffle the order of the test choices (while keeping track of the order for scoring) so that subjects cannot memorize answer order in order to cheat. Further, the program can have decision trees, so that as early determinations are made, the correct route can be navigated through the possible test frames for that particular test subject. The test may be given on a computer, though this test protocol could be done on printed material or even on TV.

Methods for Aiding Color Vision

The testing techniques described above may be employed to generate an understanding of a person's color vision. That understanding may be used to aid the development of better color vision. Based on research into the pigments of the eye's three types of color photoreceptors (cones), one explanation of red/green color blindness is that in color blind people, the sensitivity of the red and green receptors overlaps more than the sensitivity of the red and green receptors of normally-sighted people.

Figure 11:
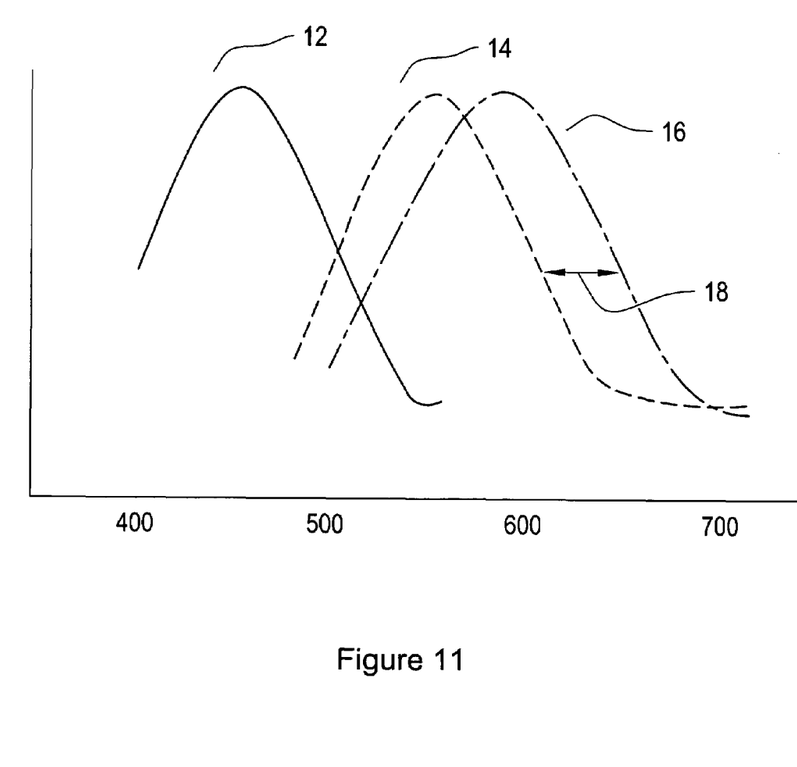
FIG. 11 depicts a graph that compare sensitivity curves for different color visions.

Turning to the Figures related to aiding color vision, shown diagrammatically in FIG. 11, is a graph that compares the sensitivity curves of a normally-sighted person's blue 12, green 14, and red 16 photoreceptors. Note that the longer wavelength sides of the green 14, and red 16, photoreceptors are separated by an amount 18.

Figure 12:
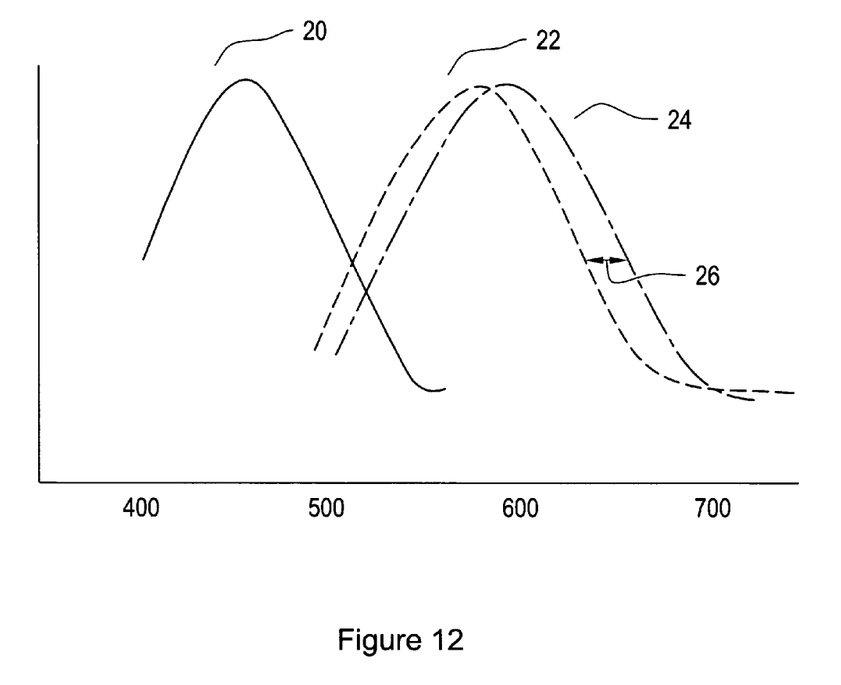
FIG. 12 depicts a further graph of sensitivity curves.
Figure 13:
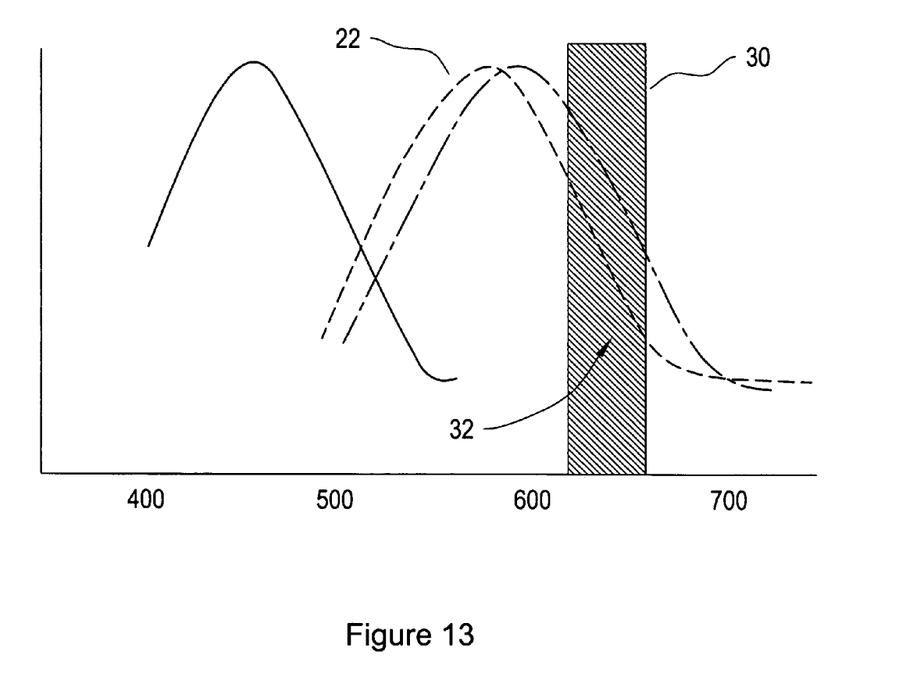
FIG. 13 depicts the effect of a blocking filter.

As is shown diagrammatically in FIG. 12, a graph compares the sensitivity curves of a red/green color blind person's blue 20, green 22, and red 24 photoreceptors. Note that in this case, the longer wavelength sides of the sensitivity curves of the green 22, and red 24, photoreceptors are separated by a lesser amount 26. This reduced separation of the two pigments' sensitivities can make it difficult for a color blind person to successfully differentiate colors, since the pigments' signals that defines the green and red color information is more confused. In a technique in accordance with the invention, as shown in FIG. 13, a blocking filter is selected such that blocking band 30 essentially blocks the long-wave toe 32, of the defective green pigment's 22, sensitivity curve.

Figure 14:
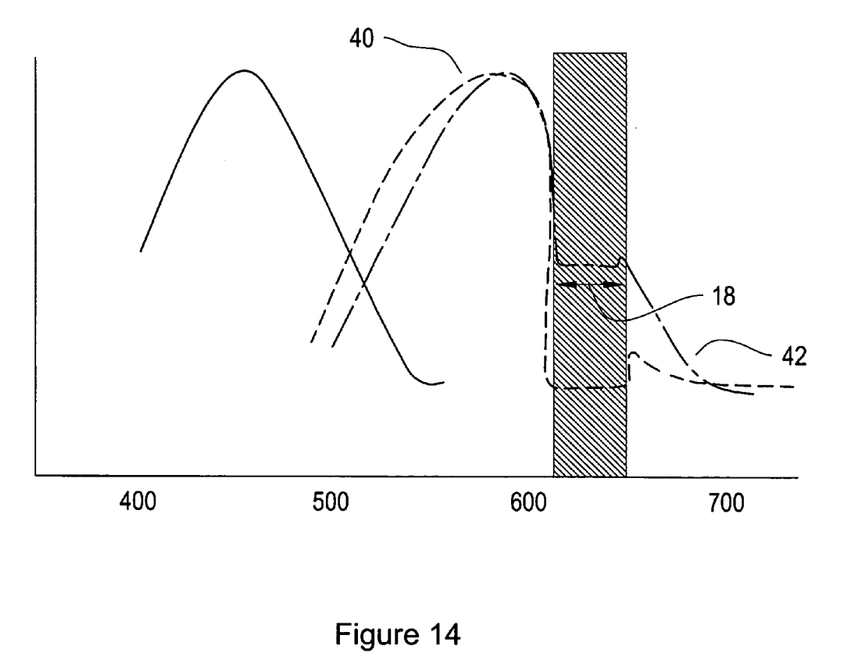
FIG. 14 depicts the effect of a blocking filter.

As is shown diagrammatically in FIG. 14, the net effect of this filter is to reestablish the amount of separation 18, between the longer wavelength sides of the now modified sensitivity curves of the green 40, and red 42, photoreceptors.

This increase separation between the green and red photoreceptors sensitivity should allow the color blind subject to more successfully differentiate between colors, since the pigments' signals that defines the green and red color information are less overlapped and thus less confused.

In a further technique in accordance with the invention, such a blocking filter can be used with a visual training computer program that tags the difference between red and green objects by encoding the colors through the use of temporal or textural cues. The use of these cues allows the different color to be tagged without changing the hue of the colors. With the enhance separation of the red and green color information from the eye's receptors, and the aid of the computer tagging to define the different colors, a color blind person can work to establish more normal color vision, i.e., to more successfully and correctly differentiate between various colors.

Figure 15:
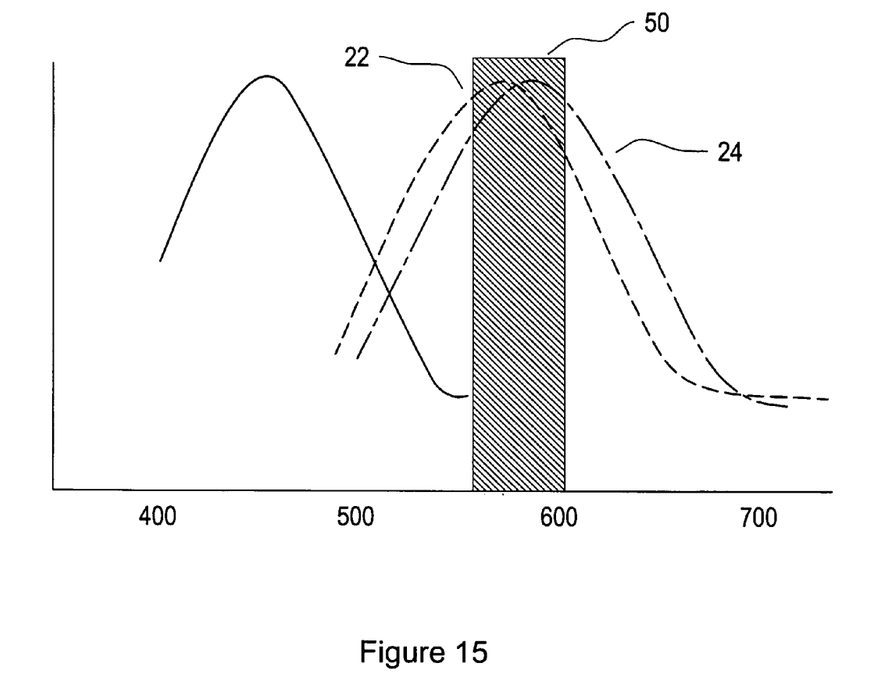
FIG. 15 depicts the effect of another blocking filter.

In yet another technique in accordance with the invention, as shown diagrammatically in FIG. 15, the blocking filter can be selected such that its blocking band 50, lies roughly in the middle of the sensitivity curves of the green 22, and red 24, pigments. In this way the section of greatest overlap is removed and the relative differential between the amplitude of the green and red signals is increased for any sample color.

The software discussed above may be realized as a software component operating on a conventional data processing system such as a Unix or Windows workstation. In that embodiment, the software may be implemented as a C language computer program, or a computer program written in any high level language including C++, Fortran, JAVA or Basic. Additionally, in an embodiment where microcontrollers or DSPs are employed, the software may be realized as a computer program written in microcode or written in a high level language and compiled down to microcode that can be executed on the platform employed. General techniques for high level programming are known, and set forth in, for example, Stephen G. Kochan, Programming in C, Hayden Publishing (1983). Those skilled in the art will know or be able to ascertain using no more than routine experimentation, many equivalents to the embodiments and practices described herein.

The invention has been described above with reference to certain exemplary embodiments. However, these systems and methods are provided as illustrative of the invention and it will be understood by one of ordinary skill in the art that the systems and methods described herein can be adapted and modified and that such other additions and modifications will not depart from the scope hereof. For example, the systems and methods described herein may be employed to test of any type of color vision, and modified for testing other aspects of a patient's visual acuity as well, including the ability to detect a wider range of colors than typical. Accordingly, it will be understood that the invention is not to be limited to the embodiments disclosed herein, but is to be understood from the following claims, which are to be interpreted as broadly as allowed under the law.

We claim:

1. A method for testing for color-impaired vision, comprising
    providing a reference image depicting a scene presented in colors selected from a selected color space,
    identifying an isochromatic line within the color space and being associated with a color vision impairment,
    generating a first test image depicting the scene of the first image presented with a color space modified to move hues along the isochromatic line,
    generating a second test image depicting the scene of the first image with a color space modified to move hues away from the isochromatic line, and
    having a patient make a visual comparison among the reference image and the first and second test images.

2. The method according to claim 1, further comprising directing the patient to compare the reference image to the first and second test images and select the test image that appears most similar to the reference image.

3. The method according to claim 1, further comprising directing the patient to compare the reference image to the first and second test images and select the test image that appears least similar to the reference image.

4. The method according to claim 1, further comprising generating a grey scale image of the scene and presenting the grey scale image to the patient for comparison.

5. The method according to claim 1, further comprising reordering the presentation of the first and second test images and having the patient repeat the visual comparison.

6. The method according to claim 5, wherein the reordering includes
    randomly reordering the first and second test images,
    repeatedly having the patient make the visual comparison, and
    determining how often the visual comparison yields similar results.

7. The method according to claim 1, further comprising generating additional test images and having the patient visually compare the additional test images to the reference image.

8. The method according to claim 1, wherein identifying the isochromatic line includes
    identifying an isochromatic line associated with a known type of color-vision.

9. The method according to claim 1, wherein identifying the isochromatic line includes
    identifying an isochromatic associated with deuteranopia.

10. The method according to claim 1, wherein identifying the isochromatic line includes
    identifying an isochromatic associated with protanopia.

11. The method according to claim 1, wherein identifying the isochromatic line includes
    randomly selecting an isochromatic line that extends at least partially through the color space.

12. The method according to claim 11, wherein
    generating a first test image includes generating the first test image with a color space modified to move hues along the partial isochromatic line.

13. The method according to claim 12, further including determining whether the patient can perceive colors along the selected partial isochromatic line.

14. The method according to claim 11, further including generating a plurality of partial isochromatic lines for constructing a line of color confusion for the patient.

15. The method according to claim 1, further comprising determining a blocking filter for increasing a separation between a first set of wavelengths and a second set of wavelengths.

16. The method of claim 15, further including applying the blocking filter to color images presented to the test taker and providing clues as to the colors being presented.

* * * * *